United States Patent [19]

Brejnik et al.

[11] 4,159,416
[45] Jun. 26, 1979

[54] ELECTRONIC CALORIE COUNTER

[76] Inventors: Carl J. Brejnik, 1327 S. 79th, Omaha, Nebr. 68124; William T. Whitlow, 217 W. Park La., Waterloo, Iowa 50701

[21] Appl. No.: 911,052

[22] Filed: May 30, 1978

Related U.S. Application Data

[63] Continuation-in-part of Ser. No. 783,974, Apr. 4, 1977, Pat. No. 4,101,071.

[51] Int. Cl.$^2$ .............................................. G06M 3/06
[52] U.S. Cl. .............................. 235/92 MT; 128/690; 235/92 T; 235/92 TF; 235/92 DP; 235/92 R; 364/415
[58] Field of Search ........ 235/92 MT, 92 DP, 92 TF, 235/92 FQ; 364/415, 705; 128/2.05 T, 2.06 F; 272/DIG. 3, DIG. 5, DIG. 6, 73, 132

[56] References Cited

U.S. PATENT DOCUMENTS

| | | | |
|---|---|---|---|
| 3,717,140 | 2/1973 | Greenwood | 128/2.06 F |
| 3,863,626 | 2/1975 | Huber | 128/2.06 F |
| 3,978,849 | 9/1976 | Geneen | 128/2.06 F |
| 3,984,666 | 10/1976 | Barron | 235/92 MT |

Primary Examiner—Joseph M. Thesz
Attorney, Agent, or Firm—Zarley, McKee, Thomte, Voorhees & Sease

[57] ABSTRACT

A calorie counter which is adapted to be constructed in the shape of a wristwatch and which includes a pulse detector for detecting the heart pulses. The calorie counter circuit consists of seven sections; time base, clock, data accumulator, data multiplier, translator, data selector and the display. The heart pulse rate is received, amplified and filtered into uniform shaped waves which are applied to the data accumulator section which totalizes the pulse count and determines the actual pulse rate which is held in a storage latch and updated at one-minute intervals. The actual pulse rate is applied to both the data multiplier section and the binary to BCD decoders. The data multiplier section includes means for presetting the calorie counter to the user's metabolism. The actual pulse rate from the data accumulator is multiplied by the preset metabolism factor and applied to the look-up memory of the translator which provides a direct calorie reading for every heart pulse rate from 40 pulses per minute to 199 pulses per minute based on the preset metabolism combination. The binary to BCD decoder converts the pulse count stored in the data accumulator latch in a binary format to a binary coded decimal format and represents the actual heart pulse rate which is applied to the data selector for numerical display. The binary coded decimal output information from the clock, translator, and binary to BCD decoder is applied to the data selector for synchronizing. Manual control is used to select the desired format of display; i.e., time, pulses per minute, or calorie total.

2 Claims, 9 Drawing Figures

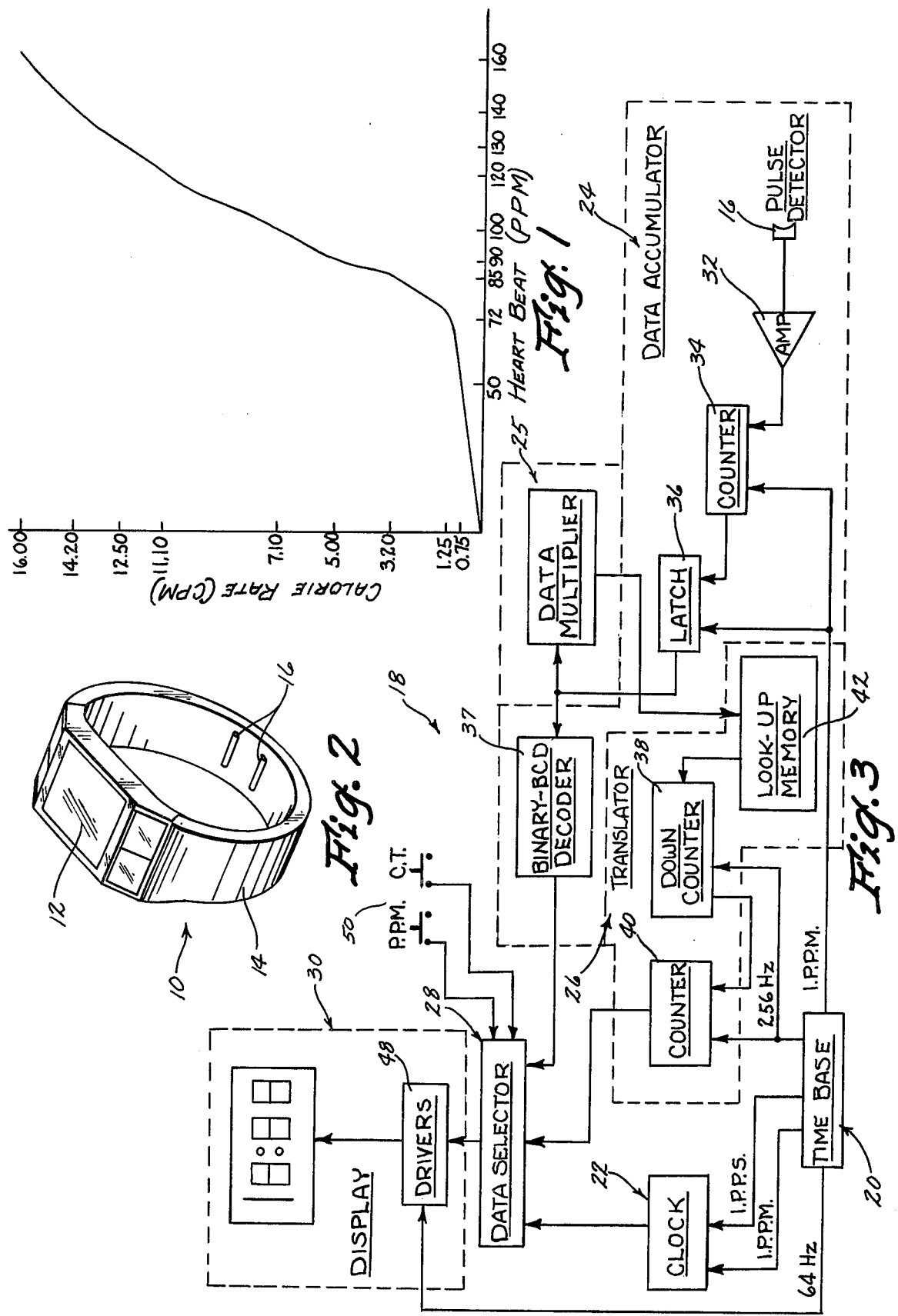

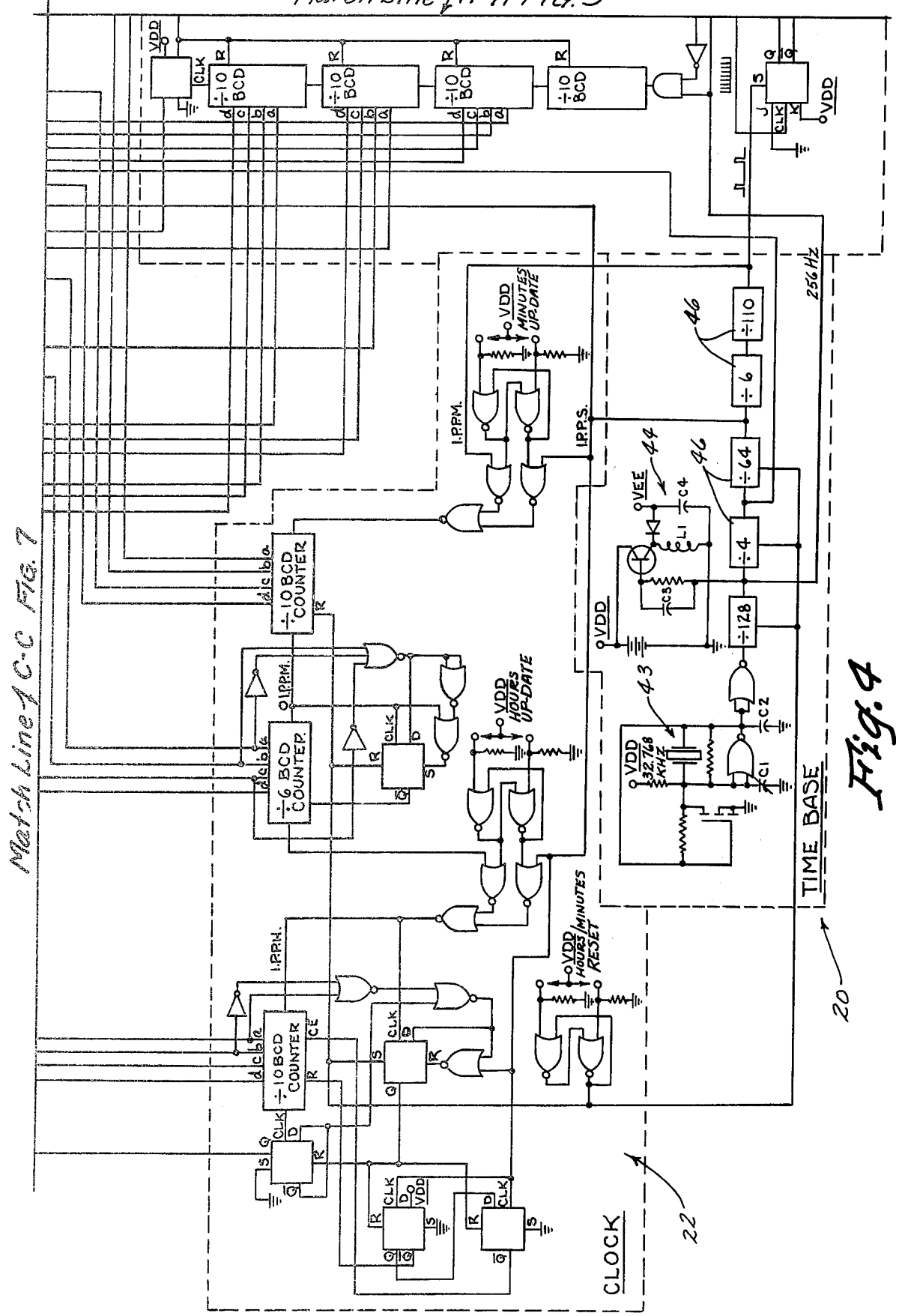

Fig. 6

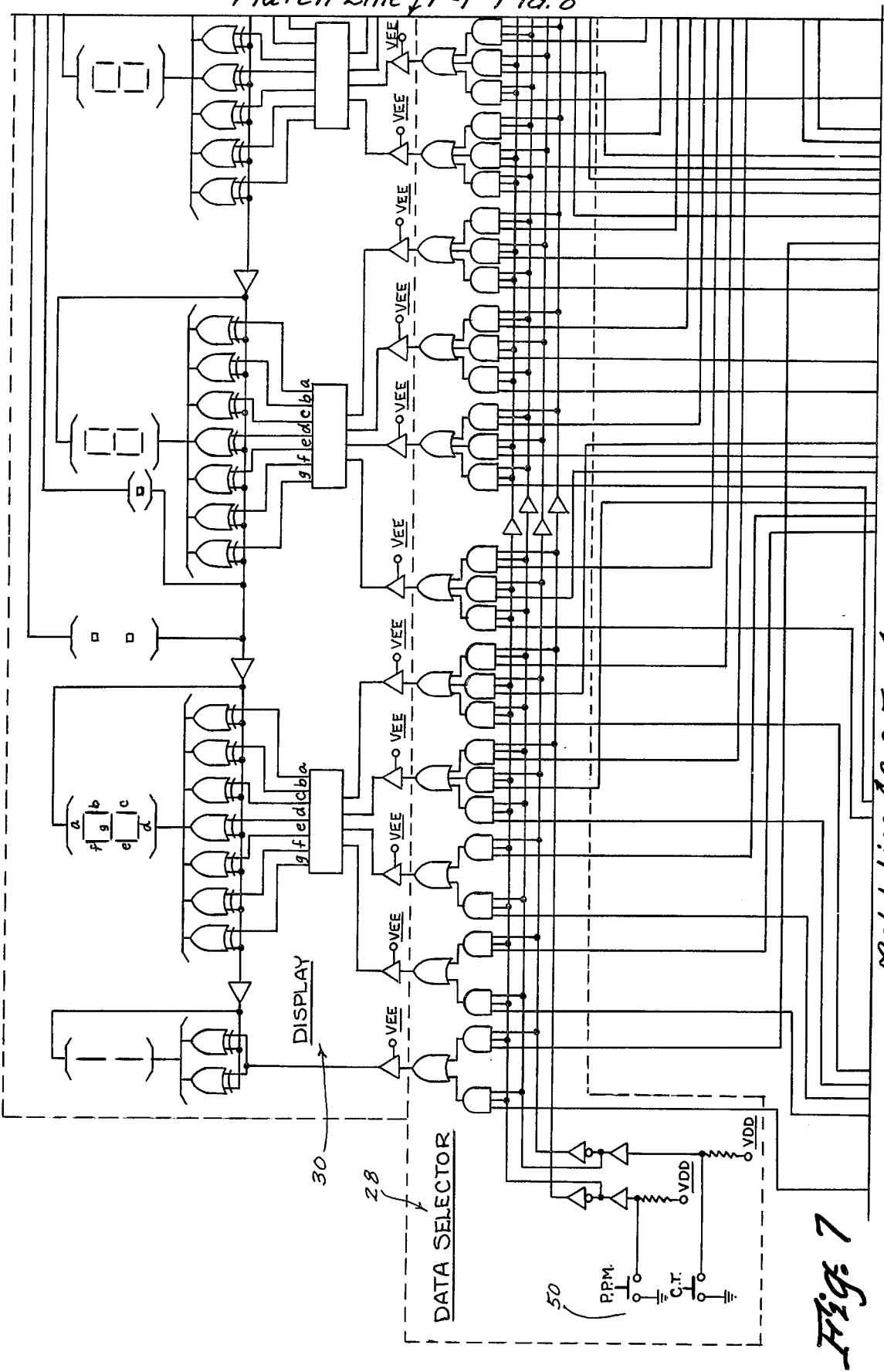

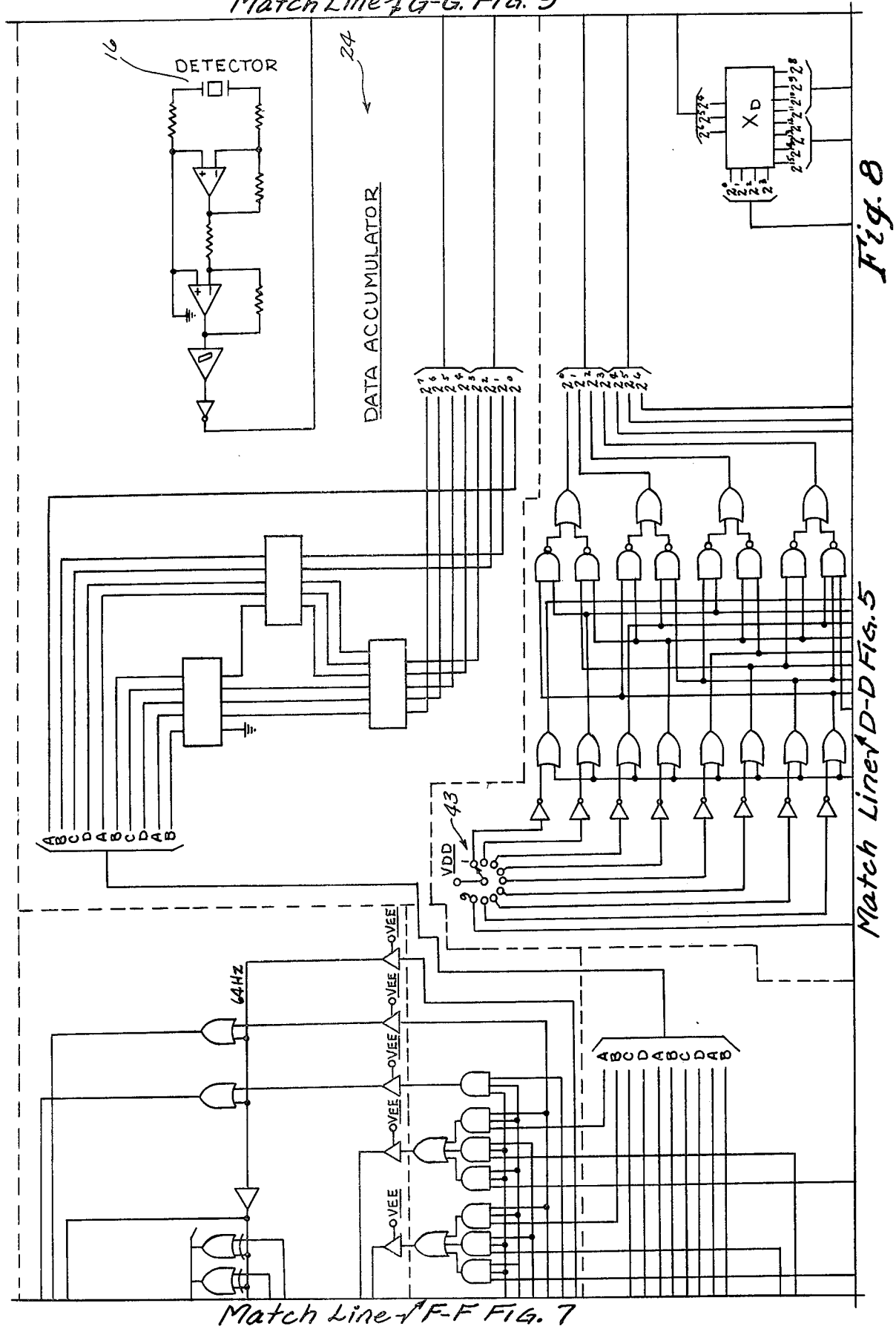

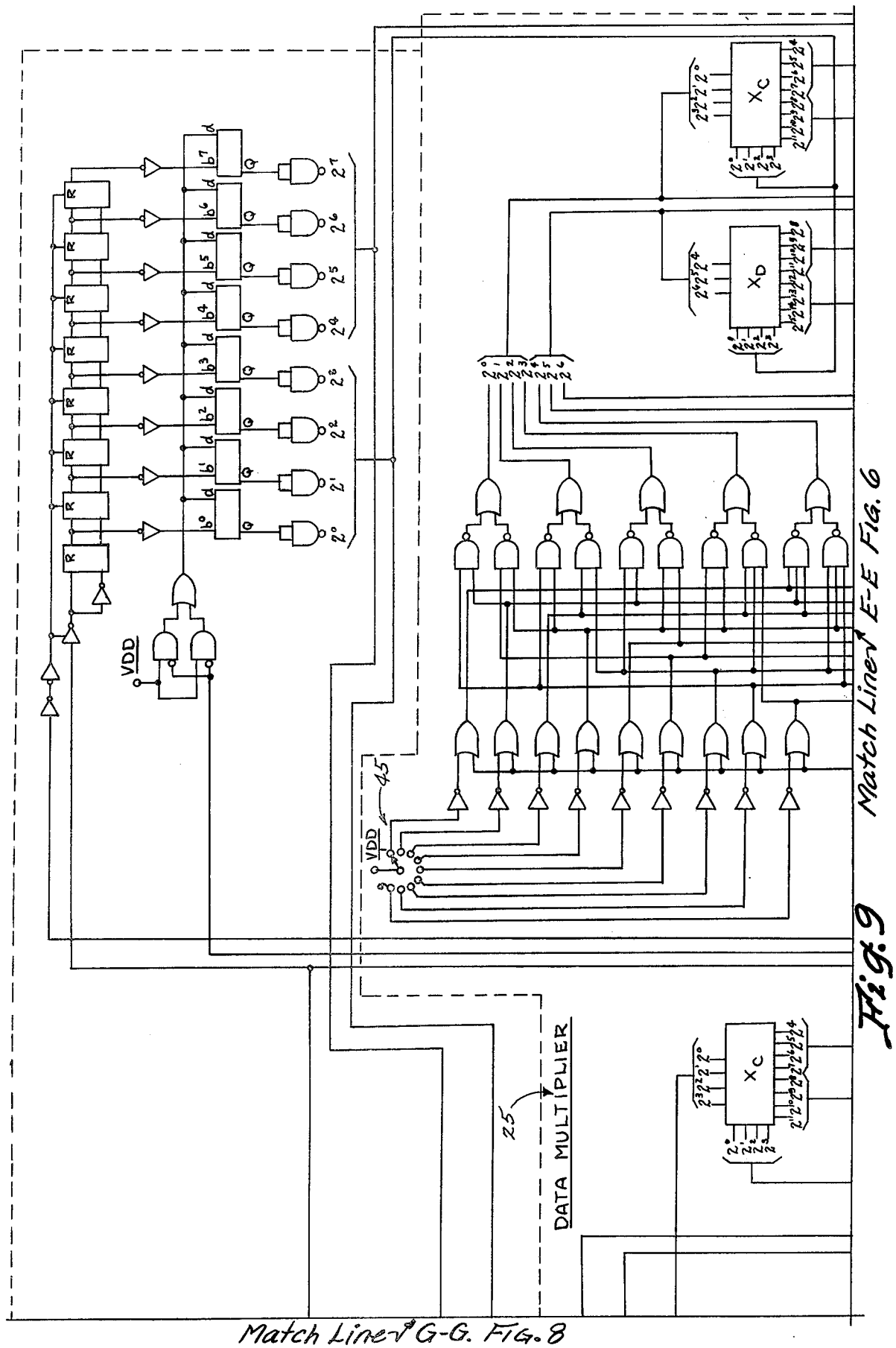

ELECTRONIC CALORIE COUNTER

BACKGROUND OF THE INVENTION

This application is a continuation-in-part application of Ser. No. 783,974 filed Apr. 4, 1977, now U.S. Pat. No. 4,101,071.

Recent studies support the theory that the pulse rate of the individual at any given time is related to the number of calories burned by the person. FIG. 1 illustrates a chart which compares the calorie burn rate versus the pulse rate. As seen in FIG. 1, the calorie burn rate is not directly proportional to the pulse rate but varies somewhat. Thus, if a person has a pulse rate of 140 pulses per minute, he will be burning approximately 16 calories per minute.

Thus it can be seen that a person will burn more calories if his heart is beating faster than if he had a slower pulse rate. Heretofore, there was no method which enabled a person to determine how many heart pulses he had experienced over a predetermined length of time which would enable him to approximate the number of calories he had consumed or burned during that same length of time.

It has also been found that the metabolic rate of a person has a direct effect of the calorie burn rate of the person. The metabolic rate may be approximately computed based upon the weight and resting pulse of the individual. The previous invention was not able to be adjusted for various metabolic rates and it is believed that the provision of such compensation permits a more accurate determination of the calorie burn rate.

Therefore, it is the principal object of the invention to provide an electronic calorie counter.

A still further object of the invention is to provide a calorie counter which detects the heart pulses and which provides a visual display of the calories per minute and the calories which have been burned since a predetermined time.

A still further object of the invention is to provide a calorie counter which may be incorporated into a wristwatch configuration.

A still further object of the invention is to provide a calorie counter having means for presetting the calorie counter to the user's metabolism.

A still further object of the invention is to provide a calorie counter which also displays the pulse rate of the user.

A still further object of the invention is to provide a calorie counter which is economical of manufacturer, durable in use and refined in appearance.

BRIEF DESCRIPTION OF THE DRAWINGS

FIG. 1 is a chart which compares the calorie burn rate versus the pulse rate:

FIG. 2 is a perspective view of the case configuration of the invention:

FIG. 3 is a block diagram of the circuitry of the invention; and

Figure 6:
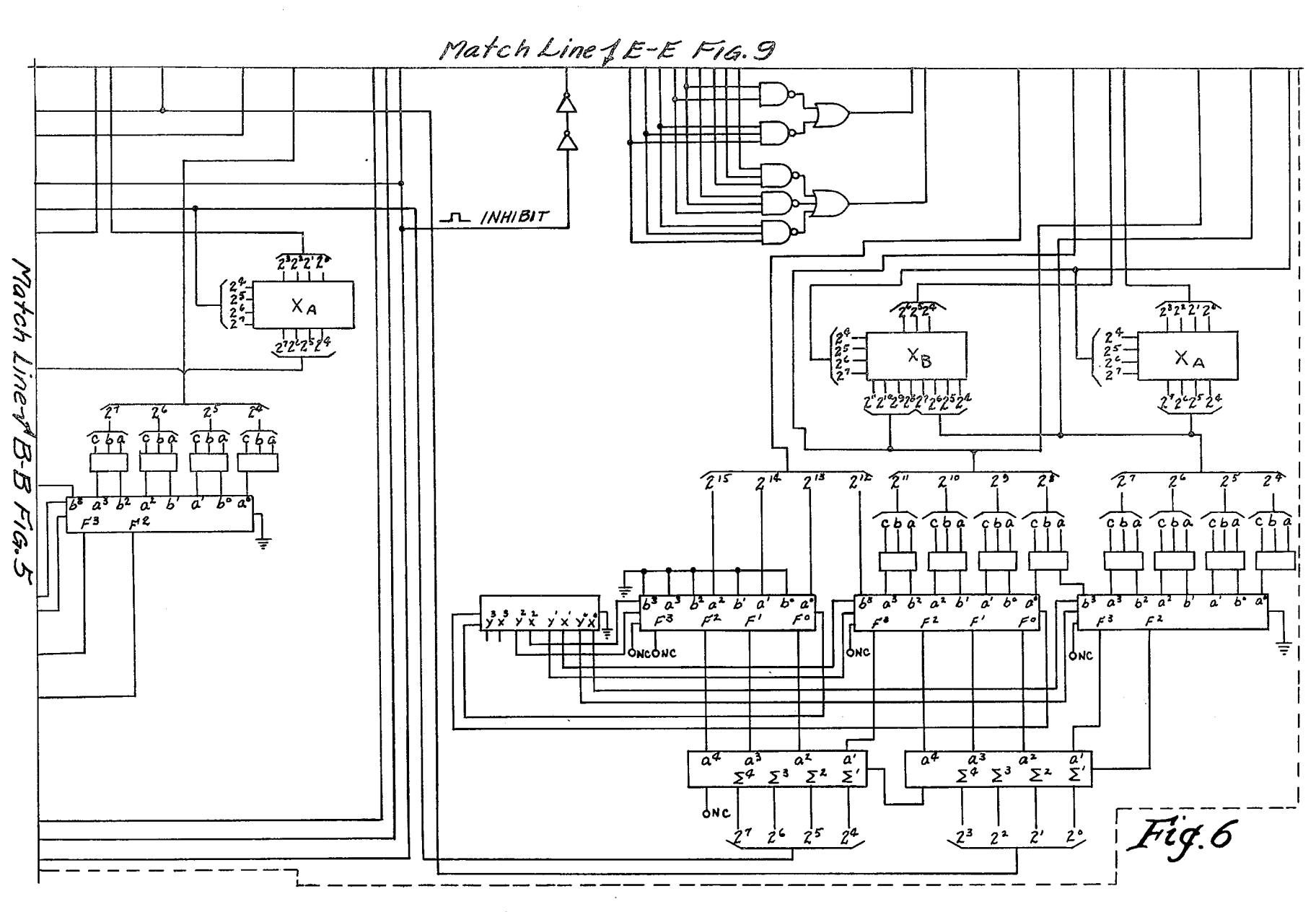

FIGS. 4–9 illustrate the electrical circuitry of the invention.

DESCRIPTION OF THE PREFERRED EMBODIMENT

Figure 5:
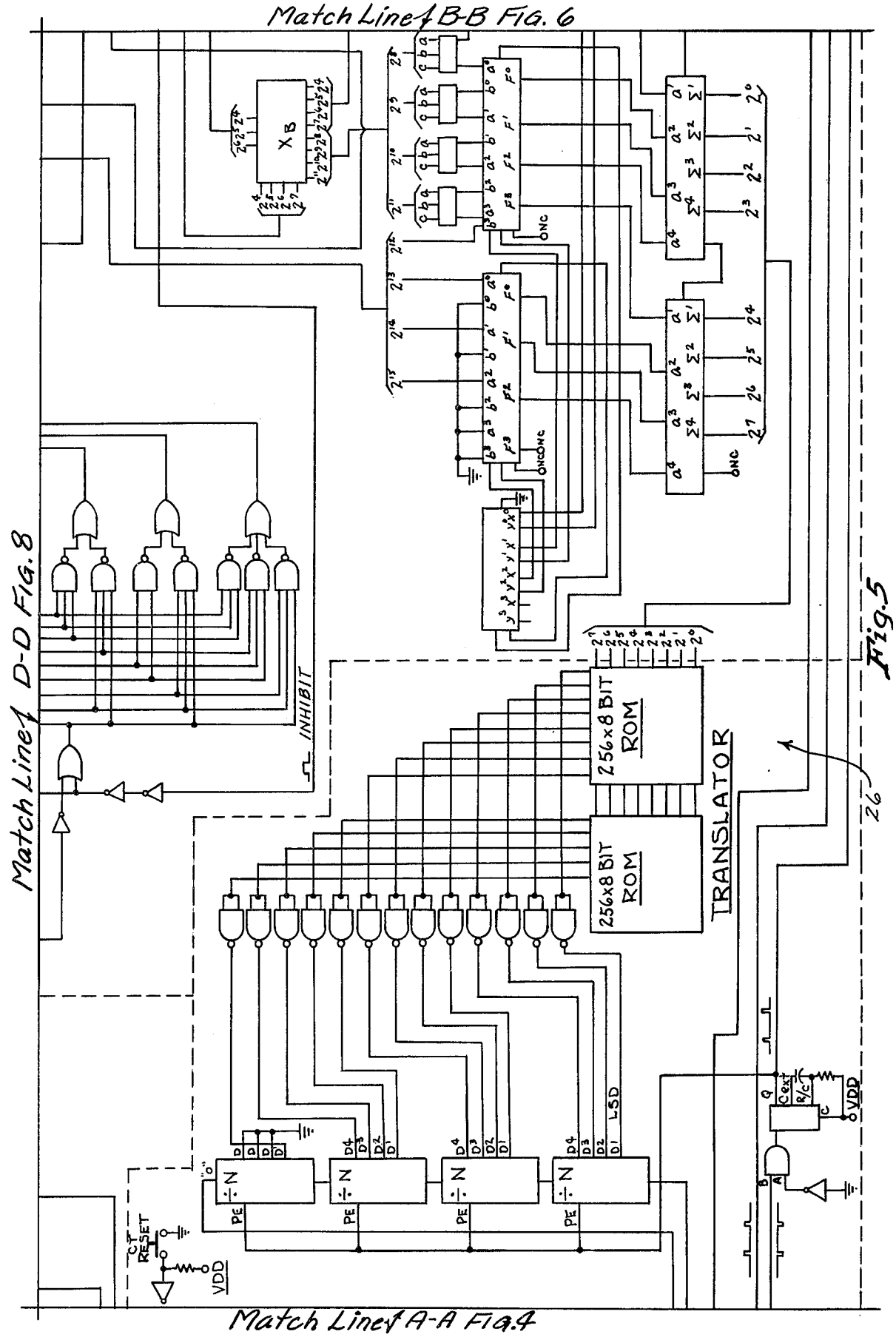

Referring to FIG. 2, the numeral 10 refers to a wristwatch device including a display area 12 and a band 14. Band 14 is provided with a conventional pulse detector 16 mounted on the interior of the band so as to detect the pulse of the wearer.

Referring to FIG. 3, it can be seen that the calorie counter circuit 18 is comprised of seven sections: (1) time base section 20; (2) clock section 22: (3) data accumulator section 24; (4) data multiplier 25; (5) translator section 26; (6) data selector section 28; and (7) display section 30.

Data accumulator 24 generally includes amplifier 32, counter 34, latch 36 and binary-BCD decoder 37. Translator 26 generally includes a down counter 38, counter 40 and look-up memory 42. Time base section 20 is comprised of a 32.768 KHz crystal oscillator 43, trimming network 44 and frequency dividers generally referred to by the reference numeral 46. Display section 30 includes a driver circuit 48. The numeral 50 refers to a manual control to permit the selection of the desired format of display.

The time base section 20 provides the clock frequencies necessary to synchronize the operation of the circuits and counter sections. These frequencies as derived from the basic 32.768 KHz oscillator are: 256 pulses/second; 64 pulses/second; 1 pulse/second; and 1 pulse/minute. The clock section 22 utilizes the 1 pulse/minute for time keeping and the 1 pulse/second for updating and setting functions. The 1 pulse/minute is divided in the decade counters to provide a binary coded decimal output for the minutes, tens of minutes and hours. Decoder logic is used to provide a 12-/hour format.

The heart pulses are received or detected, amplified, and filtered into uniform shaped waves which are applied to the data accumulator section 24. Data accumulator section 24 totalizes the pulse count for a time of one minute and thus determines the actual pulse rate. This pulse rate is held in the storage latch 36 and updated at one-minute intervals.

The actual pulse rate from the data accumulator latch 36 is applied to both the data multiplier section 25 and the binary to BCD decoders 37. The data multiplier section 25 consists of two selector switches 43 and 45 for the purpose of presetting the calorie counter to the user's metabolism. The user's metabolism will be determined in conventional fashion based upon the weight and resting pulse of the intended user. The multiplication factors range from 0.80 to 1.20 by steps of 0.05 which allow different metabolism combinations which may be preset into the system. The actual pulse rate from the data accumulator is multiplied by the preset metabolism factor and applied to the look-up memory of the translator.

The look-up memory of the translator provides a direct calorie reading for each and every pulse rate from 40 pulses per minute to 199 pulses per minute based on the preset metabolism combination. The updated calorie count for each minute at a time is preset into the divide by N down counters and accumulated in the divide by 10 binary coded decimal counters. This accumulation represents the total calorie count for a period determined by the calorie total manual present.

The binary to BCD decoder converts the pulse count stored in the data accumulator latch in a binary format to a binary coded decimal format. The BCD number represents the actual heart pulse rate which is applied to the data selector for numerical display.

The binary coded decimal output information from the clock, translator, and binary to BCD decoder is applied to the data selector for synchronizing. Manual control is used to select the desired format of display;

i.e., time, pulses per minute, or calorie total. It should be noted that time is the steady state format and all other operations are obtained only by operation of a manual selection button.

One of the three available formats is supplied to the driver circuit which converts and processes the binary coded decimal information into drive lines for the displayed numbers. The display section also provides the necessary lodging for the colon between the hours and minutes in the time format.

Thus, a person upon arising in the morning could place the calorie counter 10 on his wrist and press the calorie total manual reset. At any time during the day, the wearer simply needs to operate the manual selection button 50 to determine how many calories he has burned since he placed the watch on his wrist. Thus, if a person determined that he had not burned very many calories during the day, he may want to engage in strenuous activity before retiring so that he would burn additional calories.

Also, the wearer may determine his pulse rate at any time by simply activating the manual selection button 50 in the proper fashion.

An extremely important portion of this invention is the ability of the system to be preset corresponding to the user's metabolic rate which is dependent upon the user's weight and resting pulse. Thus, the system can be set to be used by a thin person having a high resting pulse to a heavy person having a low resting pulse or any combinations thereof.

Thus it can be seen that the invention accomplishes at least all of its stated objectives.

We claim:
1. An electronic calorie counter comprising,
   a portable pulse detector means adapted to be attached to a person's wrist and worn during daily activities for detecting the heart pulse of the person,
   electronic circuit means including an electronic counter means operatively connected to said pulse detector means for determining the pulse rate,
   a selectively adjustable data multiplier circuit means operatively connected to said electronic counter means for providing selective adjustment for a person's metabolic rate,
   electronic computer means operatively connected to said data multiplier circuit means for converting the adjusted detected pulse rate into the approximate calorie burn rate in response to programmed information in the computer means,
   said electronic computer means including means for computing the calorie burn total, for a predetermined length of time, in response to the computed calorie burn rate,
   and visual display means operatively connected to said means for computing the calorie burn total for displaying the computed calorie burn total.
2. The calorie counter of claim 1 wherein said visual display means is operatively connected to said electronic counter means for displaying the person's pulse rate.

* * * * *